United States Patent
Gilliland et al.

(10) Patent No.: US 10,959,776 B2
(45) Date of Patent: Mar. 30, 2021

(54) BIOPSY TRACT ABLATION SYSTEM FOR TUMOR SEEDING PREVENTION AND CAUTERIZATION

(71) Applicant: TRACELESS BIOPSY, LLC, Atlanta, GA (US)

(72) Inventors: Charles Gilliland, Atlanta, GA (US); Parth Patel, Clarkston, GA (US); Corey Marple, Bishop, GA (US); Carolyn Darrell, Rockville, MD (US); Kelly In, Duluth, GA (US); Sumi Marion, Atlanta, GA (US); Kirk Charles, Austell, GA (US); Brian Vanheil, Smyrna, GA (US)

(73) Assignee: TRACELESS BIOPSY, LLC, Atlanta, GA (US)

( * ) Notice: Subject to any disclaimer, the term of this patent is extended or adjusted under 35 U.S.C. 154(b) by 0 days.

(21) Appl. No.: 15/827,464

(22) Filed: Nov. 30, 2017

(65) Prior Publication Data
US 2018/0147011 A1    May 31, 2018

Related U.S. Application Data

(60) Provisional application No. 62/555,780, filed on Sep. 8, 2017, provisional application No. 62/428,467, filed on Nov. 30, 2016.

(51) Int. Cl.
*A61B 18/04* (2006.01)
*A61B 18/20* (2006.01)
(Continued)

(52) U.S. Cl.
CPC ........ *A61B 18/201* (2013.01); *A61B 17/3423* (2013.01); *A61B 18/082* (2013.01);
(Continued)

(58) Field of Classification Search
CPC ....... A61B 18/08–1492; A61B 2018/046–048; A61B 2018/087–1497;
(Continued)

(56) References Cited

U.S. PATENT DOCUMENTS 3,598,108 A * 8/1971 Jamshidi ............ A61B 10/0233
                                                         600/567
3,628,524 A * 12/1971 Jamshidi ............ A61B 10/025
                                                         600/567
(Continued)

FOREIGN PATENT DOCUMENTS

| CN | 102626329 A | 8/2012 |
| WO | 2014014336 A1 | 1/2014 |
| WO | 2014022222 A2 | 2/2014 |

OTHER PUBLICATIONS

Biomedical Tatopro Electrosurgical Thermal Ablation Electrode; 1 pg; date unknown.
(Continued)

*Primary Examiner* — Eric D. Bertram
(74) *Attorney, Agent, or Firm* — Gardner Groff & Greenwald, PC

(57) ABSTRACT

An ablation probe comprising an elongate body extending a length along a longitudinal axis from a first end to a second end, the first end extending into a housing and the second end comprising an ablation probe tip configured for insertion into a biopsy tract in a patient. In example forms, the elongate body of the ablation probe can be inserted into a patient through an existing trocar needle or biopsy access cannula following completion of a biopsy. In other example forms, the elongate body of the ablation probe defines a lumen. In one example form, the lumen contains a wire for heating the ablation probe tip, which may be composed of graphite, a resistive metal, or another electrically-resistive material. In another example form, the lumen additionally
(Continued)

contains a thermocouple or other temperature sensor for monitoring the temperature of the ablation probe tip. In any of the above example forms, use of the ablation probe to heat tissue following a biopsy effects cauterization of the tissue, stopping bleeding and reducing or preventing the seeding of additional tumors.

22 Claims, 8 Drawing Sheets

(51) Int. Cl.
| | |
|---|---|
| *A61B 17/34* | (2006.01) |
| *A61B 18/08* | (2006.01) |
| *A61B 18/12* | (2006.01) |
| *A61B 18/00* | (2006.01) |
| *A61B 10/02* | (2006.01) |
| *A61B 17/00* | (2006.01) |

(52) U.S. Cl.
CPC . *A61B 10/0233* (2013.01); *A61B 2017/00734* (2013.01); *A61B 2017/347* (2013.01); *A61B 2018/00172* (2013.01); *A61B 2018/00577* (2013.01); *A61B 2018/00595* (2013.01); *A61B 2018/00821* (2013.01); *A61B 2018/00922* (2013.01); *A61B 2018/048* (2013.01); *A61B 2018/1226* (2013.01); *A61B 2018/2005* (2013.01)

(58) Field of Classification Search
CPC . A61B 2018/00577–00595; A61B 18/20–201; A61B 10/0233; A61B 18/201; A61B 17/3423; A61B 18/082
See application file for complete search history.

(56) References Cited

U.S. PATENT DOCUMENTS

| | | | | |
|---|---|---|---|---|
| 3,886,944 | A * | 6/1975 | Jamshidi | A61B 18/082 606/30 |
| 6,296,639 | B1 * | 10/2001 | Truckai | A61B 18/082 606/41 |
| 6,506,189 | B1 | 1/2003 | Rittman, III et al. | |
| 8,414,580 | B2 | 4/2013 | Rioux et al. | |
| 8,690,868 | B2 | 4/2014 | Moorman et al. | |
| 9,877,707 | B2 | 1/2018 | Godara et al. | |
| 9,901,393 | B2 | 2/2018 | Sunenshine et al. | |
| 2003/0129382 | A1 * | 7/2003 | Treat | A61B 18/085 428/316.6 |
| 2004/0044336 | A1 * | 3/2004 | Shafirstein | A61B 18/082 606/28 |
| 2007/0161977 | A1 * | 7/2007 | Moorman | A61B 10/0233 606/33 |
| 2008/0033524 | A1 | 2/2008 | Gale | |
| 2010/0152725 | A1 * | 6/2010 | Pearson | A61B 18/12 606/33 |
| 2013/0072924 | A1 * | 3/2013 | Burgener | H01Q 1/36 606/33 |
| 2014/0257265 | A1 * | 9/2014 | Godara | A61B 18/1477 606/33 |
| 2014/0276718 | A1 | 9/2014 | Turovskiy et al. | |
| 2014/0309579 | A1 * | 10/2014 | Rubinsky | A61B 18/1492 604/21 |
| 2015/0126990 | A1 * | 5/2015 | Sharma | A61B 5/6853 606/30 |
| 2016/0100852 | A1 * | 4/2016 | Hyde | A61B 17/32056 600/309 |
| 2017/0215936 | A1 * | 8/2017 | Wallace | A61B 18/082 |

OTHER PUBLICATIONS

"Device Preventing the Dissemination of Tumor Cells Along the Needle Tract in Cancer Biopsies Using Standard Biopsy Needles and Practice"; Casinos, Mr. Tomas Escuin; Universitat Pompeu Fabra; http://knowledge.upf.edu/; 1 pg; 2015.

"Electrocautery Reduces the Risk of Hemorrhage from Biopsy"; Intracranial Endoscopy System Fiber-Optic Biopsy Needle Minimizes Hemorrhaging Risk; Truwit et al.; Office for Technology Commercialization, University of Minnesota; 3 pgs; date unknown.

"Hepatocellular Carcinoma and Liver Metastases: Clinical Data on a New Dual-Lumen Catheter Kit for Surgical Sealant Infusion to Prevent Perihepatic Bleeding and Dissemination of Cancer Cells Following Biopsy and Loco-Regional Treatments"; Izzo et al.; Infectious Agents and Cancer; 10:11; 7 pgs; 2015.

International Search Report and Written Opinion for PCT/US2017/063913; 20 pgs; dated Feb. 15, 2018.

LeVeen Needle Electrode or LeVeen CoAccess Electrode System; Thermal Ablation of Lung Cancer Radio Frequency & Microwave Ablation; www.rfalung.com/about.html; 4 pgs; 2014.

"Postbiopsy Bleeding in a Porcine Model: Reduction with Radio-Frequency Ablation-Preliminary Results"; Laeseke et al.; Radiology; vol. 227, Issue 2; pp. 493-499; May 2003.

Radiofrequency Cauterization with Biopsy Introducer Needle; Pritchard et al.; J Vasc Intery Radiol; 15 (201); pp. 183-187; Feb. 2004.

* cited by examiner

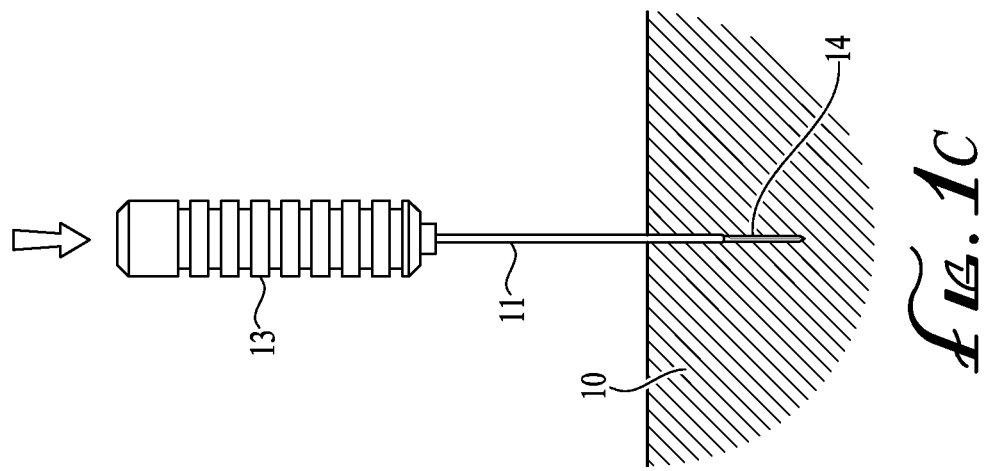
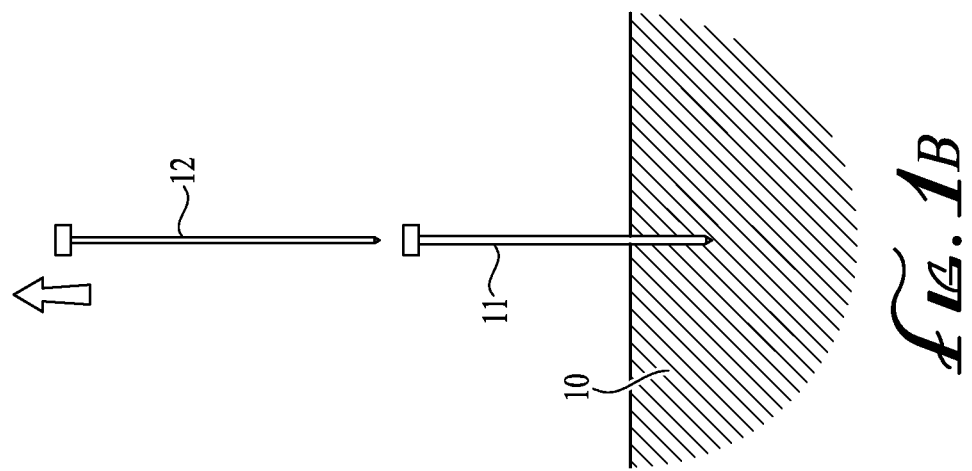
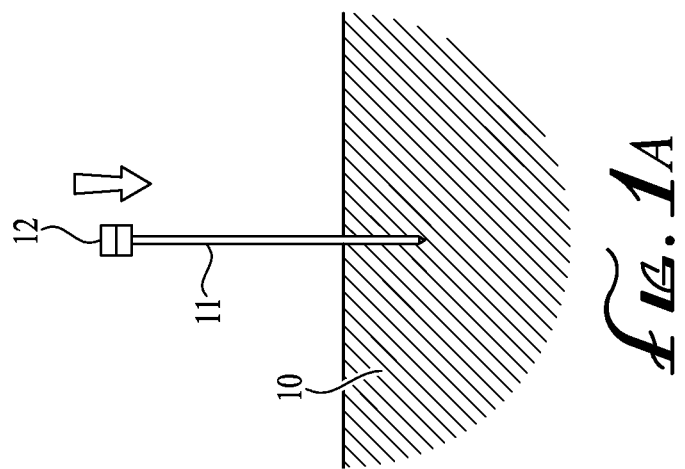

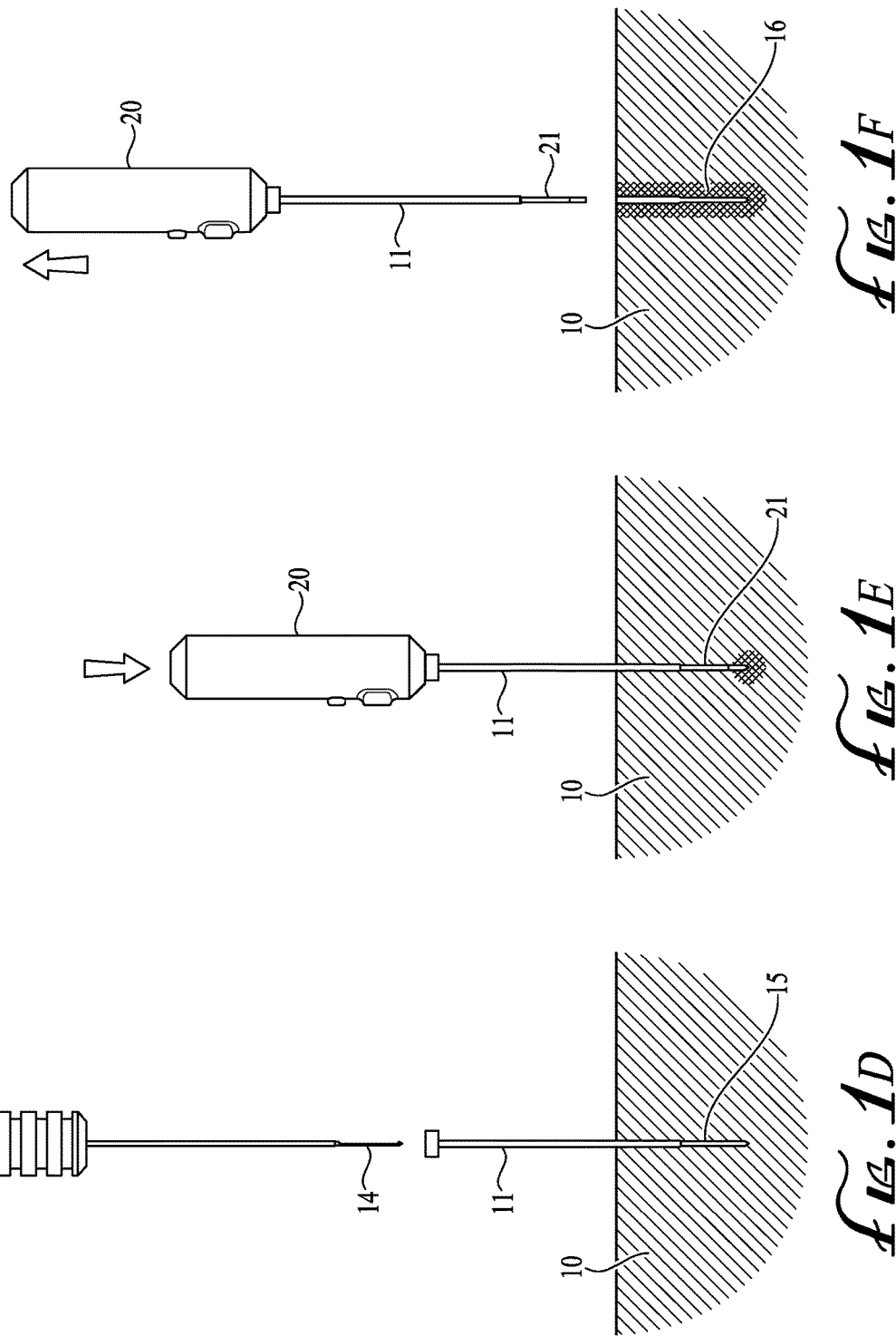

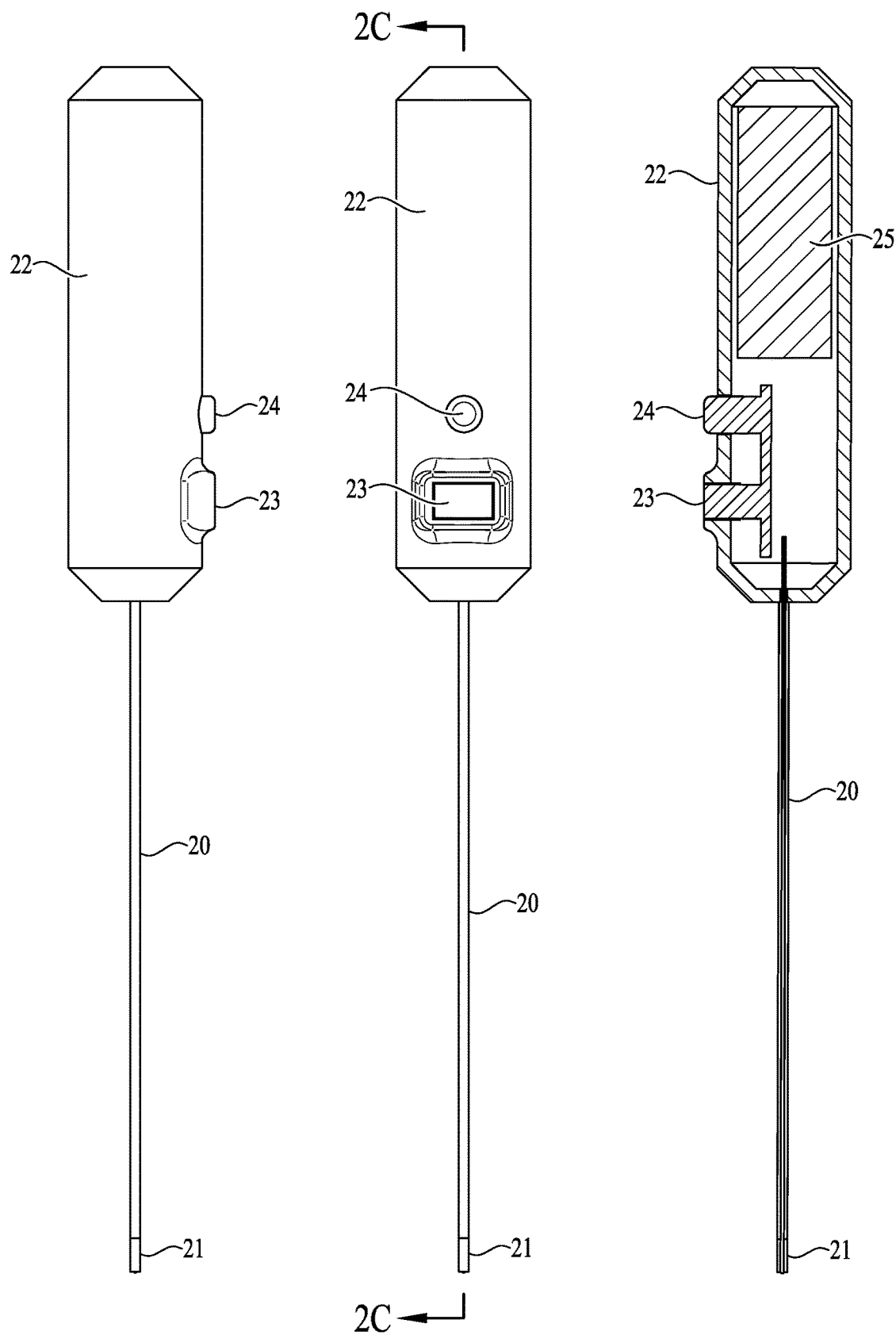

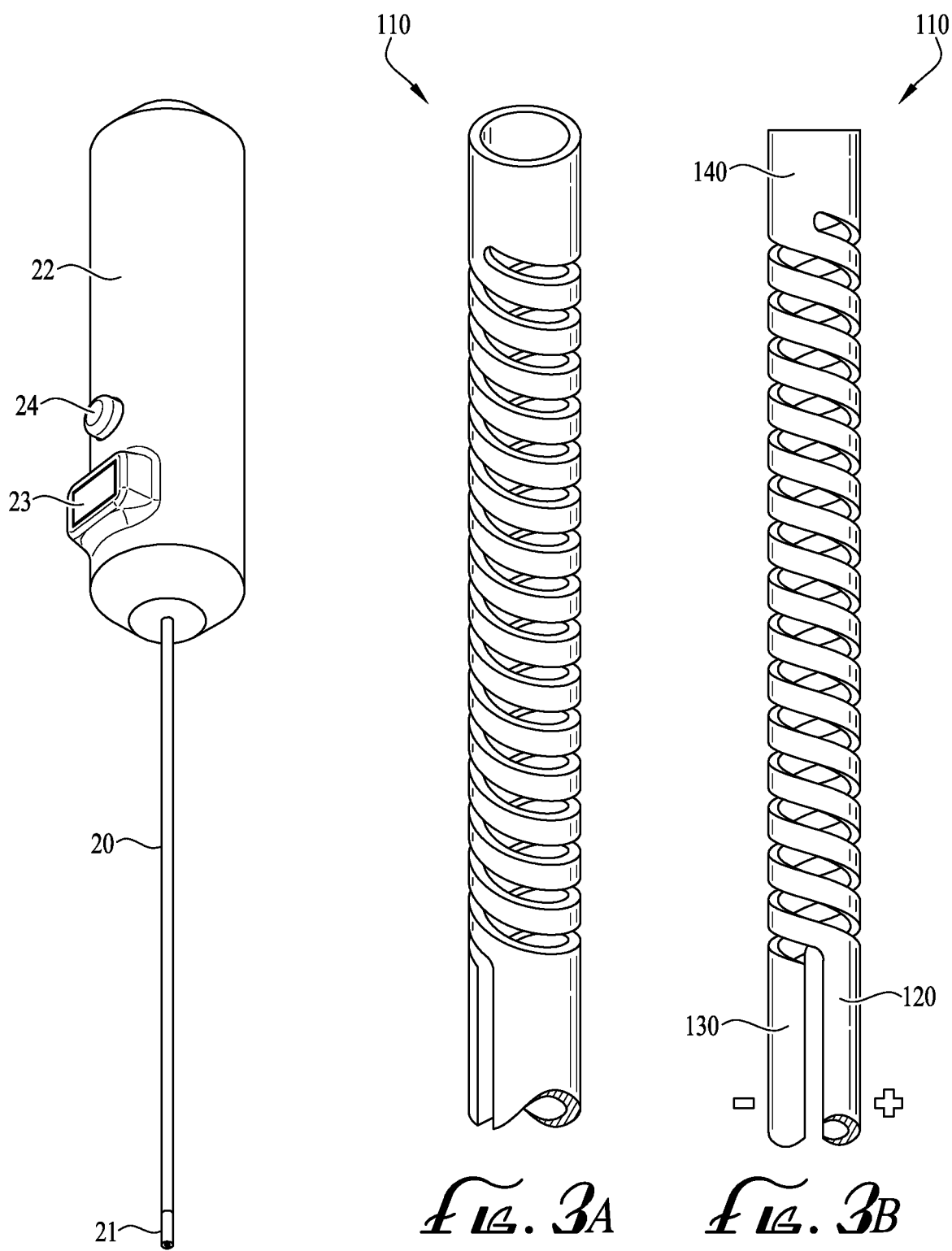

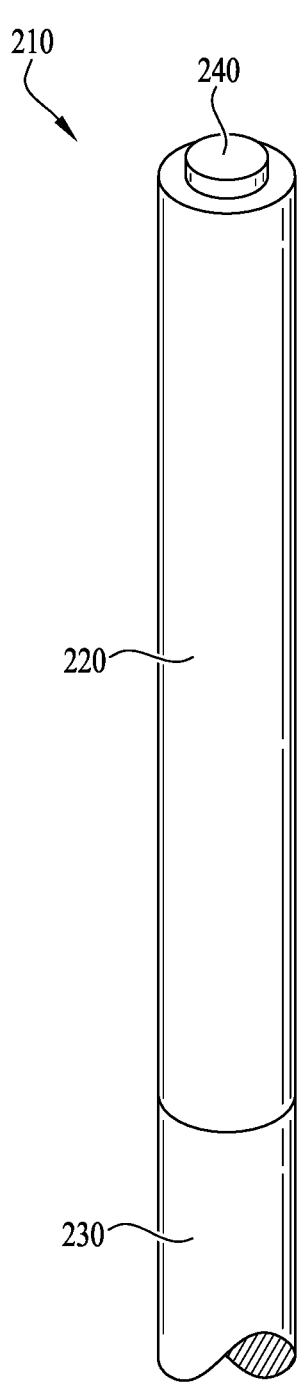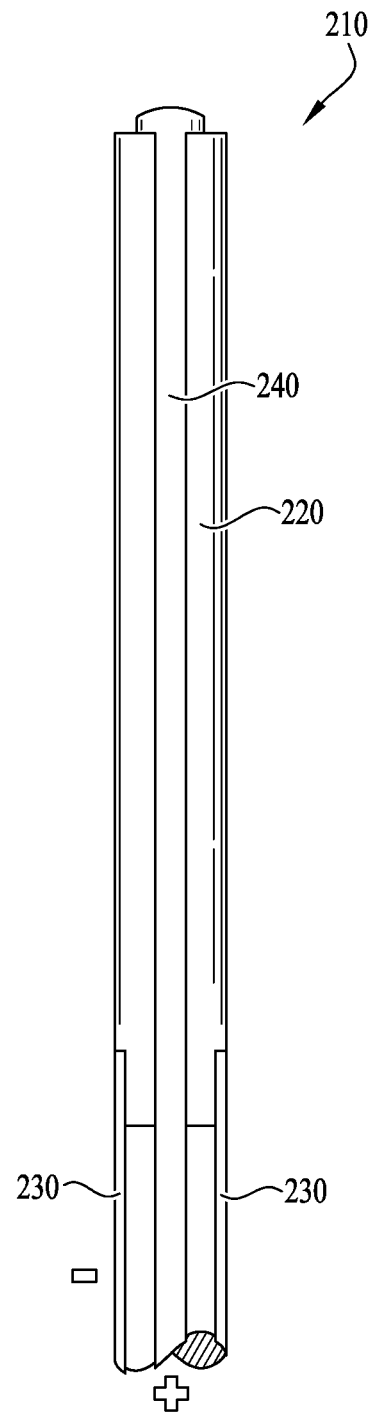

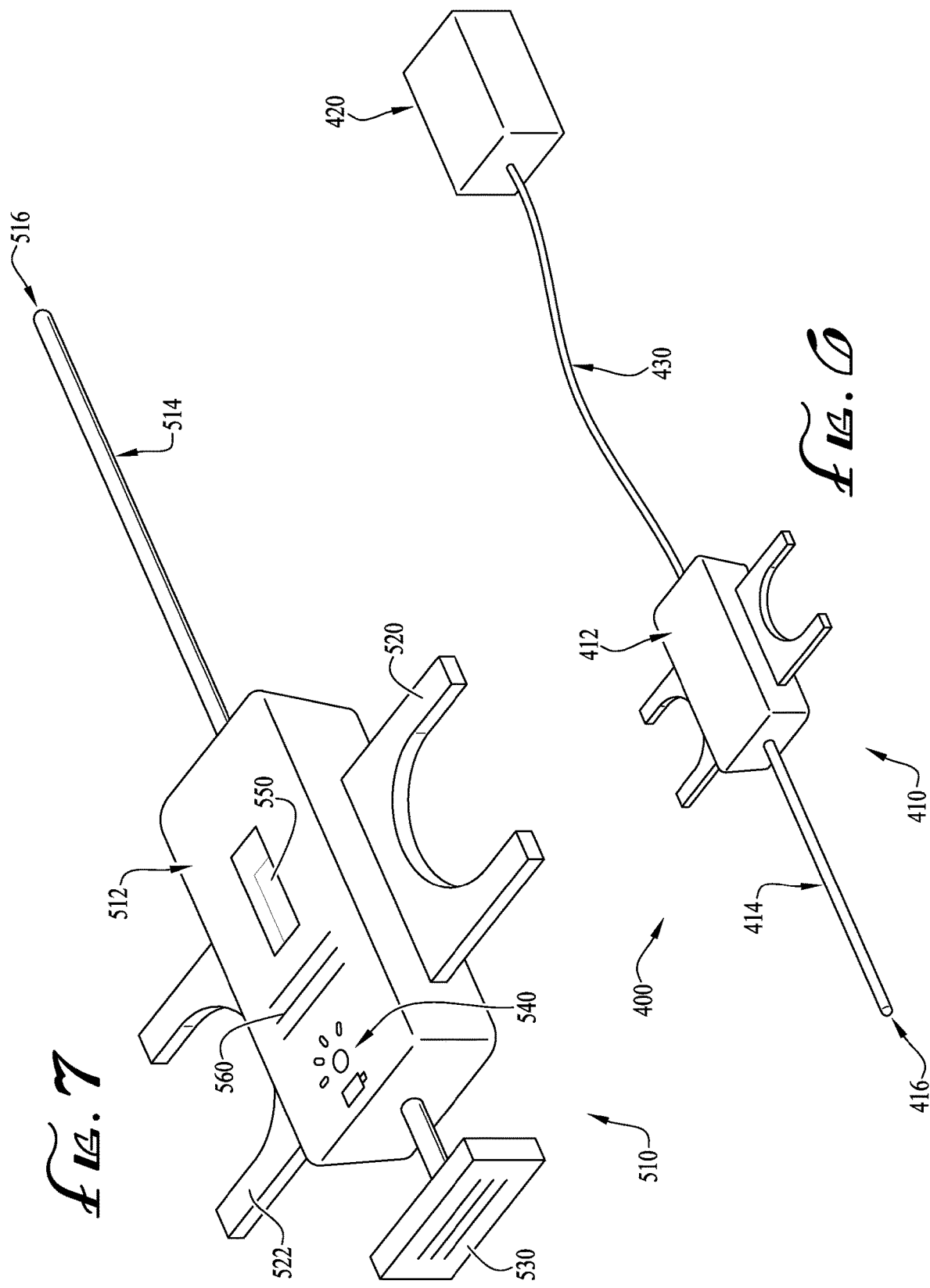

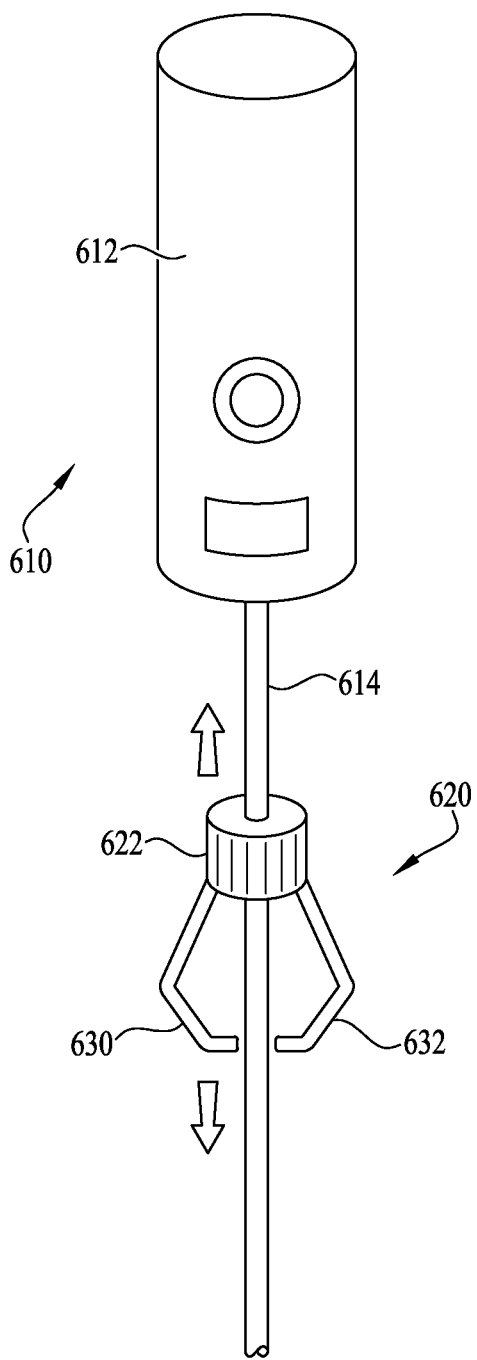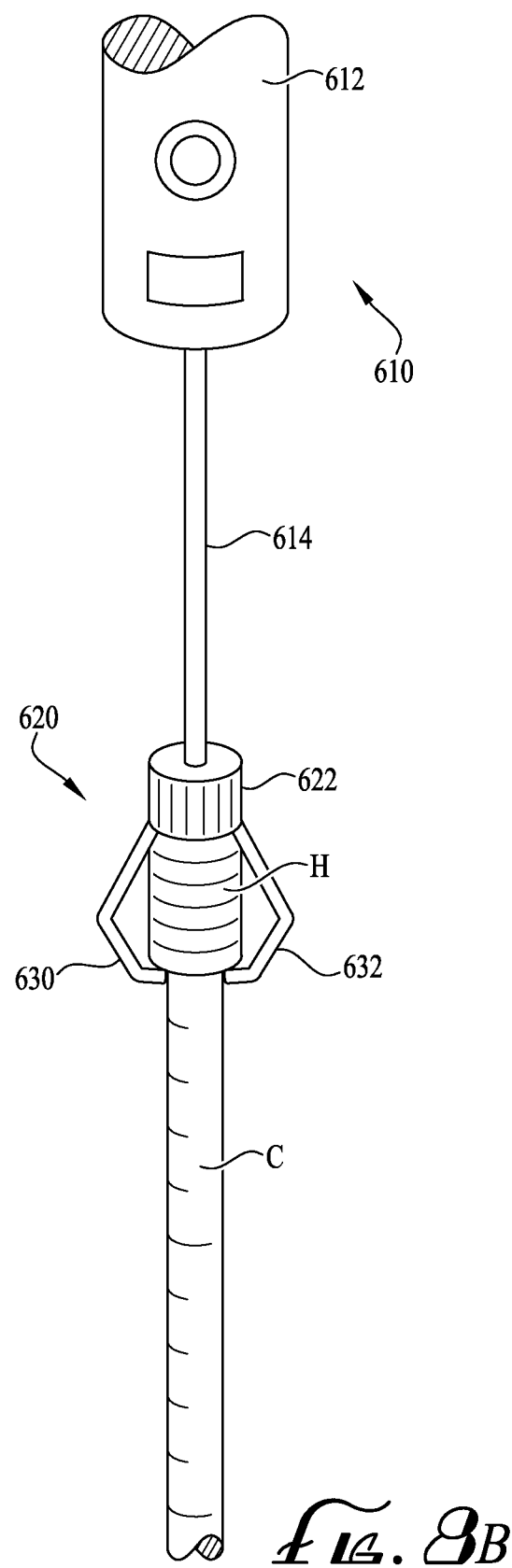
FIG. 8A
FIG. 8B

BIOPSY TRACT ABLATION SYSTEM FOR TUMOR SEEDING PREVENTION AND CAUTERIZATION

CROSS-REFERENCE TO RELATED APPLICATIONS

This application claims the priority benefit of U.S. Provisional Patent Application Ser. No. 62/555,780 filed Sep. 8, 2017, and U.S. Provisional Patent Application Ser. No. 62/428,467 filed Nov. 30, 2016, the entireties of which are hereby incorporated herein by reference.

TECHNICAL FIELD

The present invention relates generally to the field of collection of tissue samples via core needle biopsies, and more particularly to systems, apparatus and methods for ablation of a biopsy tract to prevent or reduce the potential for tumor seeding, and/or for cauterization of vascular tissue around the biopsy site.

BACKGROUND

Biopsies are performed to determine whether tumors are cancerous, to diagnose certain inflammatory conditions, and to assess organ function. In a standard core needle biopsy, a trocar needle is often inserted into the biopsy site on the patient, creating a hollow portal through which the biopsy needle is then inserted. In some instances, such as percutaneous biopsies, the biopsy needle may additionally cut small tissue samples of tissue from the patient for further analysis.

Whenever a needle is placed into the body, there is a risk of injury to the blood vessels and/or bleeding. This is a particularly strong risk during core-needle biopsies (CNBs), which are the most common biopsy procedures performed. The risk of bleeding associated with biopsies increases when larger samples and/or more samples are taken; however, diagnoses based on biopsy results are typically more accurate when larger and/or more samples are analyzed. During surgeries, cauterization is typically used to stop bleeding, but surgical cauterization methods may not be compatible with the small scale of the typical biopsy needle.

Furthermore, when the trocar needle is removed from the biopsy tract, tumor seeding may occur as cancer cells dislodge from the biopsied mass, adhere to the needle, and spread along the needle tract. Because many cancer cells lack cohesiveness, they can migrate and either grow along the tract of the needle or enter the bloodstream or interstitial fluid of nearby tissue, potentially causing cancer to spread to previously unaffected organ systems. Currently, no commercial devices are known to suitably minimize tumor seeding after biopsy, and some types of suspected cancers may not be safely biopsied due to a particularly high risk of tumor seeding.

Thus it can be seen that needs exist for a system and method that reduces or eliminates the risks of both bleeding and tumor seeding after collection of biopsy samples. Such a system and method has the potential to greatly reduce treatment costs for patients and could even prevent the conversion of a curable cancer into a metastasized, non-operable, or deadly cancer. Ideally, the system and method can be used in conjunction with existing imaging systems such as ultrasounds, CT scans, or MRI in order to guide the medical practitioner to the lesion or other area of interest. It is to the provision of system and method that meets these needs and addresses both bleeding and tumor seeding that the present invention is primarily directed.

SUMMARY

In example embodiments, the present invention provides a system that can be used with nearly all standard, commercially available trocar needles and a method incorporating an ablation probe configured to reduce or prevent bleeding and/or tumor seeding following a biopsy in a patient. In example forms, the ablation probe includes a housing that contains a power supply, internal electronic controls, or the like. The housing can optionally have openings, projections, or the like, and/or an optional power switch and indicator light. The housing may also optionally contain a power supply, a power source, and/or a temperature sensor. The ablation probe tip is located distally to the housing at the end of an elongate body (which may or may not be insulated) extending a length along a longitudinal axis from a first end to a second end, the first end extending into the housing and the second end configured to end in the ablation probe tip.

In one aspect, the present invention relates to an ablation probe. In an example form, the ablation probe defines an internal lumen extending axially from a housing for a power source, power supply, indicator light, thermocouple, and/or power switch or a combination thereof. The ablation probe is configured to fit through existing trocar needles or biopsy access cannulas such as for example those having diameters of standard gauges 16-20. In another example form, for CNBs, the ablation probe is configured to fit through trocar needles or biopsy access cannulas such as those having diameters of standard gauges from 8 to 22. In example form, the ablation probe is one gauge number higher (that is, smaller in diameter) than the trocar needle used. Distally to the housing is an ablation probe tip capable of being inserted into a biopsy tract in a patient and activated to cauterize tissue at the site of a biopsy. In example modes of use, tumor cells cannot be spread from tissue that has been cauterized, or any cell spreading is very locally minimized and preferably eliminated. In another aspect, cauterization kills tumor cells so that even if they spread through tissue upon trocar removal, they cannot seed new tumors. In further example embodiments, the ablation probe is configured to extend beyond standard biopsy throw lengths through currently existing cannulas.

In another aspect, the present invention relates an ablation probe tip. In example embodiments, only the tip of the ablation probe heats to cauterization and cancer cell elimination temperatures. In example embodiments, insulation can be provided around the trocar needle remote from the probe tip to protect the patient from tissue trauma caused by exposure to excessive heat. In example embodiments, a temperature sensor, thermocouple, or similar device can be incorporated into the device to ensure the target tip temperature is reached.

In example aspects, the ablation probe is configured to function under standard conditions for medical care such as at ambient temperature (20-25° C.) and at human body temperature (37° C.). In another aspect, the ablation probe and ablation probe tip are configured to withstand the high temperatures used for cauterization (i.e., temperatures equal to or greater than 100° C.). In some example forms, the ablation probe can be sterilized using ethylene oxide gas. In other example forms, the ablation probe can be sterilized using gamma radiation, and/or other sterilization means.

In another aspect, the present invention relates to a method and device for cauterizing tissue at the site of a biopsy. In example forms, a metal probe is heated in order to effect cauterization. In example forms, cauterization is carried out by an electrically resistive material at the tip of an ablation probe such as, for example, a graphite tip or tube or a resistive metal tip. In other example forms, heat at the tip of an ablation probe is generated through the transmission of electricity through an electrically conductive material.

In another aspect, the invention relates to an ablation probe including an elongate body extending a length along a longitudinal axis from a first end to a second end, the first end configured for coupling with a housing, and the second end comprising an ablation probe tip configured for insertion into a biopsy tract in a human or animal patient.

In another aspect, the invention relates to a method of preventing tumor seeding from a biopsy tract in a patient, the method preferably including insertion of an ablation probe through a cannula needle positioned in the biopsy tract, and heating tissue surrounding the biopsy tract with the ablation probe to a temperature therapeutically effective to kill cancer cells prior to removal of the cannula needle from the biopsy tract.

In example embodiments, the ablation probe maintains a constant temperature at, about or at least about 90° C. as it is withdrawn from the biopsy tract at a rate of at, about or no more than about 1 cm/second, to ablate any cancer cells that could potentially seed the tract. In further example embodiments, the ablation probe is a portable, entirely handheld (for example, capable of being held and operated with one hand), and optionally at least partially disposable (i.e., at least the probe tip and/or shaft portion may be disposable, while the handle or housing may be disposable or reusable) unit. In further example embodiments, the ablation probe is universally compatible with various standard commercially available cannula needles commonly utilized in biopsy procedures, without the need for specialized or proprietary biopsy equipment.

In another aspect, the invention relates to a system for reducing the potential for tumor seeding from a biopsy tract. The system preferably includes a cannula needle having a lumen extending therethrough and configured for accessing potential tumor tissue at a biopsy site within a human or animal patient's body. The system preferably also includes an ablation probe having a probe shaft configured for insertion through the lumen of the cannula needle, and further including means for heating at least a tip portion of the probe shaft to a temperature therapeutically effective to kill tumor cells around the biopsy site. In example embodiments, the means for heating optionally includes an electrical power source and an electrically resistive heating element.

In example forms, the electrically-conductive material is high-resistivity iron-chromium-aluminum alloy capable of operating at temperatures of up to 1400° C. In other example forms, the electrically-conductive material is a copper wire, a steel cylinder with a helical cut forming a path for electrical current, or a non-conductive material printed with a pattern made from a material having electrical resistance. In example forms, the electrically-conductive material is supported by a non-conductive ceramic or other non-conductive material. In example forms, along with the electrically-conductive material, the ablation probe further contains a thermocouple wire for monitoring temperature at the cauterization or ablation site.

These and other aspects, features and advantages of example embodiments of the invention will be understood with reference to the drawing figures and detailed description herein, and will be realized by means of the various elements and combinations particularly pointed out in the appended claims. It is to be understood that both the foregoing general description and the following brief description of the drawings and detailed description are exemplary and explanatory of embodiments of the invention, and are not restrictive of the invention, as claimed.

BRIEF DESCRIPTION OF THE DRAWINGS

FIGS. 1A-1F show an example system and method according to an embodiment of the present invention. In FIG. 1A, a trocar is inserted into the site on a patient from which a biopsy sample is desired. In FIG. 1B, the inner introducer needle coupled to the trocar is removed. FIG. 1C shows a biopsy gun being inserted into the trocar to biopsy tissue at the biopsy site. FIG. 1D shows removal of the biopsy gun after tissue biopsy. In FIG. 1E, an ablation probe is inserted into the trocar and heat is applied at the site of the biopsy tract, for cauterization and/or prevention of cell migration. FIG. 1F shows retraction of the trocar along with the ablation probe.

FIGS. 2A-2D show an ablation probe according to one embodiment of the present invention. FIG. 2A shows a side view of the ablation probe. FIG. 2B is a view of the front of the ablation probe including a power switch and indicator light. FIG. 2C is a cross-sectional view of the ablation probe including an internal view of the housing that holds the power supply for the probe. FIG. 2D is a perspective view of the ablation probe.

FIGS. 3A and 3B show an ablation probe tip according to an example embodiment, having a thin wall stainless steel (or other metal) cannula, cut with a helical (or otherwise configured) channel, that increases the length of an electrically conductive path, and thus increases electrical resistance to generate heat along the tip surface.

FIGS. 4A and 4B show an ablation probe tip according to another example embodiment, having a graphite (or other material of appropriate conductivity) tube at the end of a stainless steel cannula, providing electrical resistance to generate heat at the probe tip, with a copper center wire or conductor delivering electrical current to the tip of the graphite.

FIG. 6 shows an ablation probe system according to an example embodiment, including an ablation probe device, a battery pack power source, and an electrical conductor or power cord for delivering power from the power source to the probe.

FIG. 7 shows an ablation probe device according to an example embodiment.

FIGS. 8A and 8B show an ablation probe system according to another example embodiment, including a clamp or clip for engaging the hub of a biopsy cannula in order to hold the ablation tip at a fixed distance, such as approximating the throw of the biopsy needle, so that the cannula and ablation probe can be withdrawn together.

DETAILED DESCRIPTION OF EXAMPLE EMBODIMENTS

Figure 5A:
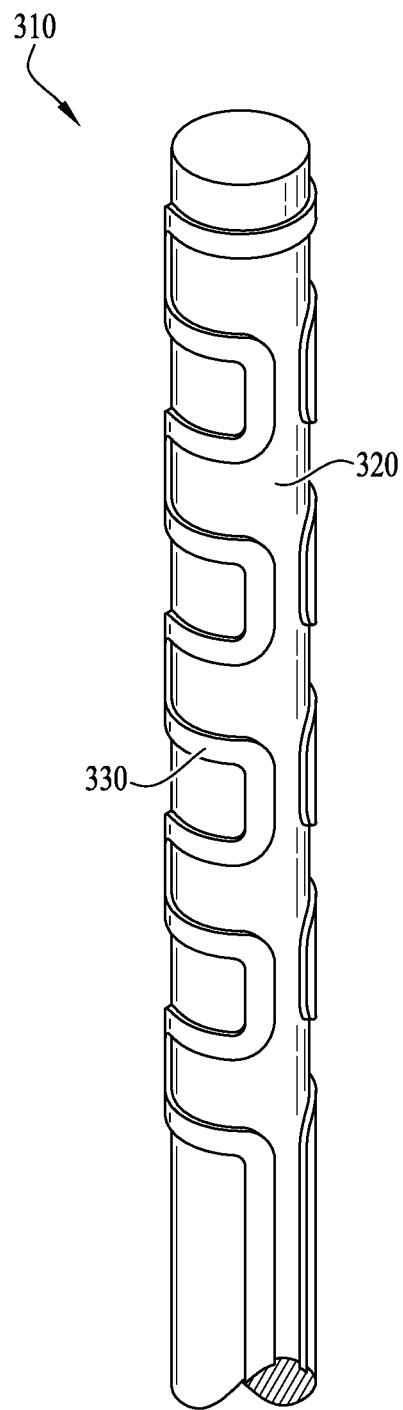
FIGS. 5A and 5B show an ablation probe tip according to another example embodiment, having a ceramic (or other non-conductive) rod printed with a heater pattern of electrically resistive material, for example applied by plating and laser ablated to form the pattern.

The present invention may be understood more readily by reference to the following detailed description taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Any and all patents and other publications identified in this specification are incorporated by reference as though fully set forth herein.

Also, as used in the specification including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

With reference now to the drawing figures, wherein like reference numbers represent corresponding parts throughout the several views, FIGS. 1A-1F show an example embodiment of a system and method of the present invention. In FIG. 1A, a site 10 of a human or animal subject's body is selected for biopsy by a medical practitioner. A trocar 11 or biopsy access cannula containing an inner introducer needle 12 is inserted through the skin and into a target tissue area at the biopsy site 10. In example embodiments, the trocar is from 15-20 gauge in size, but may be larger or smaller to suit the intended application. The probe length (excluding housing) can be variable and in example embodiments, ranges from about 5 cm to about 25 cm. In one embodiment, a single probe is envisioned with 25 cm length in order to work through substantially any commercially-available biopsy cannula. In this embodiment, the probe may additionally be fitted with an adjustable Luer lock or clasp that can slide up and down the length of the ablation probe for the purpose of adjustability to various lengths of trocar. In alternative embodiments, different probe lengths can be constructed, specific to existing trocar lengths. In still other example embodiments, the throw length can be set by the user depending on the position of the cannula or trocar tip as well as the sample being collected. Example dimensions for the probe are provided in Table 1.

TABLE 1

Probe Dimensions

| Gauge | Diameter (mm) |
|---|---|
| Diameter | |
| 15 | 1.45 |
| 16 | 1.29 |
| 17 | 1.15 |
| 18 | 1.02 |
| 19 | 0.91 |
| 20 | 0.81 |
| Length (cm) | |
| Minimum | 5 |
| Maximum | 25 |

In example embodiments, the active tip for ablation can be variable, from a shorter length of 1-2 mm to up to 30 mm. In FIG. 1B, following insertion, inner introducer needle 12 is removed from trocar 11. FIG. 1C shows a biopsy gun 13, for example a standard commercial biopsy gun, being inserted into the trocar with biopsy gun tip 14 extending through trocar 11 and into the tissue to be sampled. A tissue sample is obtained and removed according to standard protocol; following which, as shown in FIG. 1D, biopsy gun 13 is removed from trocar 11, leaving biopsy tract 15. FIG. 1E shows insertion of the ablation probe 20 into site 10 through trocar 11 with ablation probe tip 21 extending down into the biopsy tract. Ablation probe 20 is activated to generate heat energy at least at and around the probe tip sufficient to cauterize the tissue surrounding the biopsy tract to minimize or prevent bleeding, and/or to kill or attenuate potential cancer or tumor cells at the biopsy site to an extent sufficient to prevent cell migration away from the biopsy site. FIG. 1F shows removal of ablation probe 20 including ablation probe tip 21, wherein the trocar 11 remains attached to ablation probe 20 and is withdrawn from site 10 along with ablation probe 20, leaving behind cauterized and/or treated biopsy tract 16. In some embodiments, the ablation probe is configured to attach to and remove the trocar or biopsy access cannula as the ablation probe is withdrawn, or alternatively for separate retraction and removal.

FIGS. 2A-2D show several views of an ablation probe according to an example embodiment of the present invention. FIG. 2A is a side view of ablation probe 20 having housing 22 that comprises a power supply, internal electronic controls, timer circuits, one or more sensors, and the like. Housing 22 can optionally have openings, projections, or the like for one or more accessories such as an optional power actuator switch 23 and/or indicator light(s) 24 (for example, timer lights, temperature indication lights or gauges, battery level indicator, etc.). Housing 22 may also optionally contain a power supply, a power source, electronic controls, and/or a temperature sensor; or alternatively such components can be located in a remote housing in electronic communication with the probe 20. Housing 22 can be made of any medical grade material such as, for example, acrylonitrile-butadiene-styrene (ABS), polycarbonate, or polypropylene and can be formed by typical plastic shaping processes such as, for example, injection molding. Ablation probe tip 21 is located distally to the housing at the end of an elongate body extending a length along a longitudinal axis from a first end to a second end, the first end extending into housing 22 and the second end configured to end in tip 21. In example embodiments, the ablation probe can be operated without a wired connection to an external power source. In one embodiment, the power source is an onboard battery such as, for example, a 9V battery. In other embodiments, the battery can be contained in an external, removable battery pack, or the probe may be connected to a remote AC power source. In some embodiments, the ablation probe system is portable. The ablation probe is optionally configured as a single-use disposable device; or alternatively may be configured for sterilization and reuse. FIG. 2B is a front view of ablation probe 20 showing the same external features as FIG. 2A. FIG. 2C is a cross-sectional view of ablation probe 20 showing the internal relationships among the positions of power switch 23 and/or indicator light 24 as well as casing 25 holding such elements as a power supply, temperature control module, and other features. FIG. 2D is a perspective view of ablation probe 20.

In example embodiments, the elongate body of the ablation probe defines a lumen. In particular embodiments, the lumen is configured to house one or more wires. In some embodiments, the one or more wires include a thermocouple to monitor the temperature of the ablation probe tip, a wire for heating the ablation probe tip, or both. In example embodiments, the wire for heating the ablation probe tip is composed of a high-resistivity iron-chromium-aluminum alloy capable of operating at temperatures of up to 1400° C. In particular embodiments, the elongate body of the ablation probe is constructed from metal such as, for example, 304 stainless steel. Various configurations of the ablation probe body, lumen, and tip are within the scope of the present invention. In any of the various embodiments, the materials from which the ablation probe, and particularly the probe tip, are constructed are preferably biocompatible.

FIGS. 3A and 3B show an example embodiment of an ablation probe tip 110 configuration. The tip of the elongate body of the ablation probe comprises a thin walled stainless steel or other electrically conductive metal cannula cut into a dual helix or two-conductor helical pattern to form a first electrically conductive path from a positive conductor base 120, and a second electrically conductive path from a negative conductor base 130 to a connector tip or bridge 140 in electrically conductive contact via the two helical conductor paths with both the positive and negative bases, to generate heat at and around the ablation probe tip by electrical resistance. The helix pattern increases the length of the conductive path, and thereby increases the probe tip's electrical resistance for generating heat at and around the probe tip. Optionally, the hollow cannula configuration of the probe tip allows a temperature probe (thermocouple) to be installed in the lumen thereof to monitor temperature during use. In example embodiments, a ceramic or other non-conductive central core material is optionally provided to support the helically cut metal cannula.

FIGS. 4A and 4B show another example embodiment of an ablation probe tip 210. In the depicted embodiment, the ablation probe tip 210 comprises a graphite (or other material of appropriate electrical conductivity/resistance) tip or tube 220 extending from the end of the stainless steel cannula 230 of the probe body. The graphite tip or tube 220 provides electrical resistance to produce the desired degree of heat when in use. A copper wire or other electrical conductor 240 extends through the graphite tip or tube 220, with the wire 240 connected to one terminal (positive or negative) of an electrical power source, and with the stainless steel cannula 230 of the probe body connected to the other terminal (negative or positive) to generate heat by electrical resistance in and around the tip 210. In example embodiments, the graphite tip 220 can be bonded to the copper wire 240 with adhesive, or alternatively the copper wire can comprise an expanded retainer tip and be attached under tension to retain the graphite tip in place on the cannula of the ablation probe.

Figure 5B:
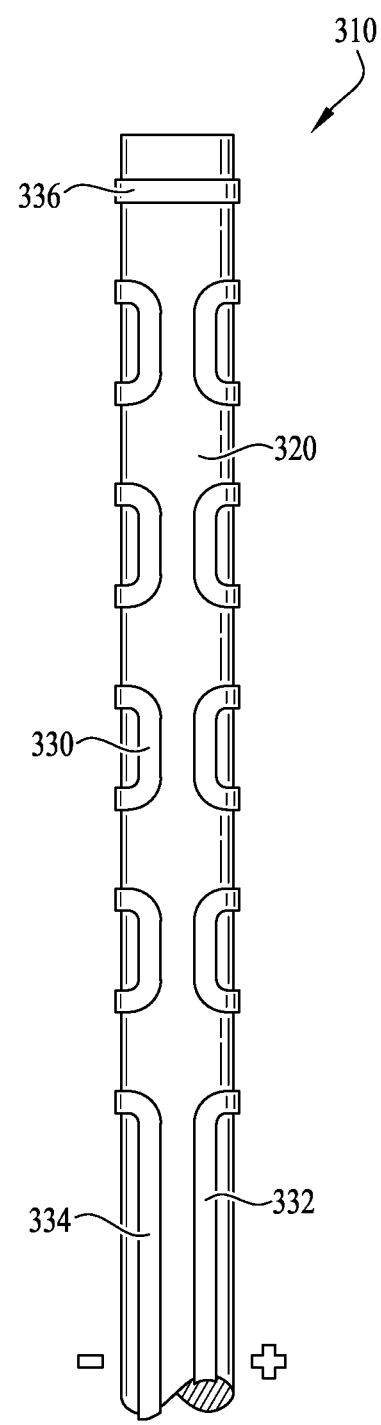

FIGS. 5A and 5B show another example embodiment of an ablation probe tip 310. In the depicted embodiment, the ablation probe tip 310 comprises a ceramic (or other electrically non-conductive material) rod 320 printed with a heater pattern 330 of electrically resistive material. In example embodiments, the heater pattern can be applied using plating and then laser ablated, or alternatively can be formed by alternate fabrication processes. The heater pattern 330 includes a first conductive path portion 332 in electrical connection with the positive side of a power source, a second conductive path portion 334 in electrical connection with the negative side of the power source, and a bridging conductive path portion 336 connecting the first and second path portions. In example embodiments, the ceramic rod 320 can optionally be hollow to allow a temperature probe or thermocouple to be installed in the lumen thereof to monitor temperature.

FIG. 6 shows an ablation probe system 400 according to an example embodiment of the invention. The system 400 generally comprises an ablation probe 410, a power source 420, and a connection cord 430 extending between the probe and the power source. The ablation probe 410 comprises a housing 412, a probe body 414, and a probe tip 416. In example embodiments, the power source 420 comprises one or more batteries for providing DC electrical power or a transformer for delivering power from an external AC electrical power source. The connection cord 430 preferably comprises wires, cable or other electrical conductors for delivering power and/or control signals between the ablation probe 410 and the power source 420. FIG. 7 shows additional details of an ablation probe 510 according to an example embodiment of the invention, comprising a housing 512, a probe body 514, and a probe tip 516. The housing 512 optionally further comprises finger grips 520, 522, an actuator plunger or switch 530, a battery life and power indicator light or gauge 540, a temperature indicator 550, and a sound transducer 560 coupled to a timer for indicating a treatment time duration.

FIGS. 8A and 8B show an ablation probe 610 according to another example embodiment of the invention, comprising a housing or handle 612, a probe body or shaft 614, and an adjustable clip or clamp 620 configured to slide along the probe shaft to engage the hub H of a cannula needle C, so that the ablation probe and the cannula can be withdrawn from the biopsy site together at the same time with the ablation tip at a fixed distance beyond the hub of the cannula needle, such as a distance approximating the length of the biopsy throw. In example embodiments, the clamp 620 optionally comprises a screw clamp 622 configured to slide up and down coaxially along the shaft 614 (as indicated by the directional arrows in FIG. 8A) for selective positioning by the practitioner to adjust to different cannula lengths, and releasably engageable to lock the clamp at one or more selected positions along the shaft corresponding to a cannula length depth setting. The clamp 620 optionally also comprises an opposed pair of spring-loaded arms or fingers 630, 632 extending from the screw clamp 622 for selective engagement of the hub H of the cannula needle C, as shown in FIG. 8B. The spring-loaded arms or fingers 630, 632 are preferably formed of an elastically resilient material capable of retracting apart from one another to engage over the hub H, and return biased inwardly to contract and retain the hub in secure engagement. The free ends or tips of the spring-loaded arms or fingers 630, 632 are optionally tapered obliquely inward to receive and engage the hub H. Engagement of the cannula hub H with the clamp 620 and locking of the screw clamp 622 in position on the shaft 614 allows a practitioner to withdraw the cannula C from the biopsy site together with the ablation device 610 simultaneously with a single operation.

In example embodiments, the invention further comprises a medical procedure method or process for cauterizing a biopsy tract in a patient and/or preventing cell migration or tumor seeding. The method comprises the steps of inserting an ablation probe, for example according to any of the embodiments disclosed herein, through a trocar or biopsy access cannula, activation of the probe to generate sufficient heat in and around the biopsy site to effect the cauterization process and/or to prevent cell migration or tumor seeding, and withdrawal of the ablation probe, leaving behind a cauterized biopsy tract that does not bleed and/or that prevents migration of cells and potential seeding of tumor cells. In example embodiments, tissue at or around substantially all or at least a portion of the biopsy tract is heated by contact with the ablation probe to a temperature of at least 90° C. In other embodiments, the tissue at or around substantially all or at least a portion of the biopsy tract is heated to a temperature of about 100° C. In still other embodiments, the tissue surrounding the ablation probe tip can be heated to 180° C. or even up to 1200° C. In particular embodiments, the probe tip is maintained at 90 degrees C. or greater while it is retracted at a rate of 1 cm per second. This methodology ensures death of greater than 99.99% of tumor cells along the biopsy tract. In example embodiments, cauterization of the biopsy tract and prevention of cell migration is accomplished by delivery of heat through an ablation probe. In alternate embodiments, cauterization and prevention of cell migration is accomplished through an ablation probe delivering steam, laser irradiation, or direct contact with electrically conductive materials. In example embodiments, cauterization simultaneously acts to stop patient bleeding from the biopsy site and kills or inactivates cancer cells to prevent tumor seeding. In example embodiments, the probe can be withdrawn at different rates depending on physician or technician concerns. In one aspect, if bleeding is the primary concern, retraction of the probe can be performed slowly (for example, at a rate of 1 cm every 5 seconds). In another aspect, if tumor seeding is the primary concern, retraction can be faster (e.g., 1 cm per second). In still another aspect, probe withdrawal rate is selected by the physician or technician balancing concerns such as bleeding, tumor seeding, and patient comfort. In any of these aspects, the probe can be maintained at a constant, elevated temperature during withdrawal to ensure complete cauterization of the biopsy tract and prevention or minimization of potential tumor seeding.

In example embodiments, only the tip of the ablation probe is heated. In particular embodiments, thermal insulation can be provided around the shaft of the ablation probe to ensure that only tissue at the biopsy site and desired tract length is cauterized and to protect the patient from additional tissue trauma caused by extreme heat. In alternate embodiments, the entire metal or conductive portion or surface of the ablation probe is heated.

In example embodiments, the ablation probe including the housing can be sterilized using any common sterilization method including, but not limited to, exposure to ethylene oxide gas or gamma radiation, or heat sterilized using an autoclave. In alternate embodiments, the probe tip and/or the hollow metal body portion of the ablation probe is/are configured to be removable from the housing for disposable single use application. In still further embodiments, the entire ablation probe, including the probe tip, body and housing are disposable for single use application.

While the invention has been described with reference to example embodiments, it will be understood by those skilled in the art that a variety of modifications, additions and deletions are within the scope of the invention, as defined by the following claims.

What is claimed is:

1. An ablation probe comprising:
   a housing configured for hand-held use, the housing comprising an onboard battery power source and a power actuator switch; and
   an elongate body extending a length along a longitudinal axis from a first end to a second end, the first end coupled to the housing, and the second end comprising an ablation probe tip comprising an electrically-resistive heating element electrically connected to the onboard battery power source, the electrically-resistive heating element comprising an electrically-resistive material applied in a pattern onto an electrically non-conductive rod portion of the ablation probe tip, the pattern defining at least one conductive path portion for heating the ablation probe tip to a tumor-seeding prevention temperature sufficient to prevent cell migration and potential tumor seeding in a biopsy tract in a patient, wherein the pattern is applied by plating the electrically-resistive material onto the electrically non-conductive rod portion, and laser ablating a portion of the applied electrically resistive material from the electrically non-conductive rod portion; and
   wherein the elongate body comprises a thermally non-conductive material between the first end and the ablation probe tip whereby only the ablation probe tip is heated to the tumor-seeding prevention temperature upon activation.

2. The ablation probe of claim 1, further comprising a temperature sensor for the ablation probe tip, and wherein the housing further comprises an indicator light responsive to the ablation probe tip reaching the tumor-seeding prevention temperature.

3. The ablation probe of claim 1, wherein the elongate body of the ablation probe defines a lumen.

4. The ablation probe of claim 3, wherein the lumen is configured to house one or more wires electrically connecting the onboard battery power source to the electrically-resistive heating element.

5. The ablation probe of claim 1, wherein the ablation probe is configured for insertion into a biopsy tract through a standard commercial trocar or biopsy access cannula.

6. The ablation probe of claim 5, wherein the trocar or biopsy access cannula is from 6-22 gauge, and wherein the ablation probe has a maximum external dimension less than 6-22 gauge.

7. The ablation probe of claim 5, wherein the ablation probe is configured to attach to and remove the trocar or biopsy access cannula as the ablation probe is withdrawn.

8. The ablation probe of claim 1, further comprising a clamp mounted to the elongate body and configured for engaging a hub of a cannula to allow retraction of the cannula from the biopsy tract together with the ablation probe.

9. The ablation probe of claim 1, wherein at least the elongate body portion is disposable.

10. The ablation probe of claim 1, wherein the tumor-seeding prevention temperature is at least 1200° C.

11. A system for reducing the potential for tumor seeding from a biopsy tract, the system comprising:
   a cannula needle having a lumen extending therethrough and configured for accessing potential tumor tissue at a biopsy site within a human or animal patient's body; and
   an ablation probe comprising a housing configured for hand-held use, the housing comprising an onboard battery power source and a power actuator switch, the ablation probe further comprising a probe shaft coupled to the housing and configured for insertion through the lumen of the cannula needle, the probe shaft comprising an ablation probe tip having an electrically-resistive heating element electrically connected to the onboard battery power source, the electrically-resistive heating element comprising an electrically-resistive material applied in a pattern onto an electrically non-conductive rod portion of the ablation probe tip, the pattern defining at least one conductive path portion for heating the ablation probe tip to a tumor-seeding prevention temperature sufficient to prevent cell migration and potential tumor seeding in a biopsy tract in a patient, the pattern comprising a first conductive path in electrical connection with a positive terminal of the onboard battery power source, a second conductive path in electrical connection with a negative terminal of the onboard battery power source, and a bridging portion connecting the first conductive path and the second conductive path, wherein at least one of the first conductive path and the second conductive path define an undulating wave pattern having a plurality of wave segments with alternating axially and transversely directed wave segment portions; and wherein the probe shaft comprises a non-conductive portion extending between the housing and the ablation probe tip whereby only the ablation probe tip is heated to the tumor-seeding prevention temperature upon activation.

12. The system of claim 11, wherein the cannula needle comprises a hub, and wherein the ablation probe comprises a clamp member for engaging the hub of the cannula needle and allowing the cannula needle to be withdrawn from the biopsy site simultaneously together with the ablation probe.

13. The system of claim 11, wherein the tumor-seeding prevention temperature is at least 1200° C.

14. An ablation probe comprising:
a housing configured for hand-held use, the housing comprising an onboard battery power source and a power actuator switch; and
an elongate probe shaft extending a length along a longitudinal axis from a first end portion coupled to the housing to a second end portion, the probe shaft comprising an electrically non-conductive portion extending from the first end portion to the second end portion, and the second end portion comprising an electrically-resistive graphite probe tip electrically connected to the onboard battery power source to heat the electrically-resistive graphite probe tip to a tumor-seeding prevention temperature sufficient to prevent cell migration and potential tumor seeding in a biopsy tract in a patient;
wherein the electrically-resistive graphite probe tip comprises a graphite tube and an electrically-conductive wire extending through the graphite tube.

15. The ablation probe of claim 14, further comprising a temperature sensor and an indicator light on the housing responsive to the graphite probe tip reaching the tumor-seeding prevention temperature.

16. The ablation probe of claim 14, wherein the first end portion of the elongate probe shaft comprises a stainless steel cannula in electrically conductive contact between a first terminal of the battery power source and a proximal end of the graphite tube.

17. The ablation probe of claim 16, wherein the electrically-conductive wire extends through the stainless steel cannula, the electrically-conductive wire being in electrically conductive contact between a second terminal of the battery power source and a distal end of the graphite tube.

18. The ablation probe of claim 14, wherein the ablation probe is configured for insertion into a biopsy tract through a standard commercial trocar or biopsy access cannula.

19. The ablation probe of claim 18, wherein the trocar or biopsy access cannula is from 6-22 gauge, and wherein the ablation probe has a maximum external dimension less than the gauge of the trocar or biopsy access cannula.

20. The ablation probe of claim 18, wherein the ablation probe is configured to attach to and remove the trocar or biopsy access cannula as the ablation probe is withdrawn.

21. The ablation probe of claim 14, further comprising a clamp mounted to the elongate body and configured for engaging a hub of a cannula to allow retraction of the cannula from the biopsy tract together with the ablation probe.

22. The ablation probe of claim 14, wherein the tumor-seeding prevention temperature is at least 1200° C.

* * * * *